US008676306B2

(12) United States Patent  (10) Patent No.: US 8,676,306 B2
Qu et al.  (45) Date of Patent: *Mar. 18, 2014

(54) METHODS AND SYSTEMS FOR ANALYZING T-WAVE ALTERNANS

(75) Inventors: Fujian Qu, Sunnyvale, CA (US); Riddhi Shah, Mountain View, CA (US)

(73) Assignee: PaceSetter, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/563,522

(22) Filed: Jul. 31, 2012

(65) Prior Publication Data

US 2013/0030313 A1 Jan. 31, 2013

Related U.S. Application Data

(63) Continuation of application No. 12/456,628, filed on Jun. 18, 2009, now Pat. No. 8,255,043, and a continuation-in-part of application No. 12/340,352, filed on Dec. 19, 2008, now Pat. No. 8,457,727.

(60) Provisional application No. 61/073,666, filed on Jun. 18, 2008.

(51) Int. Cl.
*A61B 5/0452* (2006.01)

(52) U.S. Cl.
USPC ............................................ 600/515

(58) Field of Classification Search
None
See application file for complete search history.

(56) References Cited

U.S. PATENT DOCUMENTS

| 5,861,009 | A  | 1/1999  | Armstrong       |
|-----------|----|---------|-----------------|
| 7,171,258 | B2 | 1/2007  | Goode           |
| 7,336,995 | B2 | 2/2008  | Armoundas et al.|
| 2004/0267142 | A1 | 12/2004 | Paul         |
| 2005/0010122 | A1 | 1/2005  | Nearing et al.|
| 2007/0049835 | A1 | 3/2007  | Goode        |
| 2009/0192398 | A1 | 7/2009  | Zhou         |
| 2009/0318822 | A1 | 12/2009 | Qu           |

FOREIGN PATENT DOCUMENTS

WO  WO 2005/002435  1/2005

OTHER PUBLICATIONS

Online Real Time Detection of Atrial Fibrillation, Lu, Sheng et al, Department of Biomedical Engineering, Medicine (Cardiology), State University of New York, Stony Brook, Heart Rhythm 2007, 16 pgs.
Non-Final Office Action mailed Jan. 31, 2012 Related U.S. Appl. No. 12/456,628.
Notice of Allowance mailed May 25, 2012 Related U.S. Appl. No. 12/456,628.
Non-Final Office Action mailed Oct. 28, 2011 Related U.S. Appl. No. 12/340,352.
Non-Final Office Action mailed Apr. 6, 2012 Related U.S. Appl. No. 12/340,352.

*Primary Examiner* — Brian T Gedeon
(74) *Attorney, Agent, or Firm* — Theresa Rayner; Steven M. Mitchell

(57) ABSTRACT

Embodiments of the present invention relate to implantable systems, and methods for use therein, that can detect T-wave alternans and analyze the detected alternans to provide information regarding cardiac instabilities and predict impending arrhythmias.

10 Claims, 5 Drawing Sheets

METHODS AND SYSTEMS FOR ANALYZING T-WAVE ALTERNANS

PRIORITY CLAIM AND CROSS REFERENCE TO RELATED APPLICATIONS

This application is a Continuation application of and claims priority and other benefits from U.S. patent application Ser. No. 12/456,628, entitled "Methods and Systems for Analyzing T-Wave Alternans," filed Jun. 18, 2009, now U.S. Pat. No. 8,255,041 which claims the benefit of U.S. Provisional Application No. 61/073,666, entitled "Methods and Systems for Analyzing T-Wave Alternans." filed Jun. 18, 2008, the specification of which are expressly incorporated herein by reference in their entirety. This application is also a Continuation-In-Part application of and claims priority and other benefits from U.S. patent application Ser. No. 12/340,352, entitled "Monitoring Variation Patterns in Physiological Parameters Associated with Myocardial Instability," filed Dec. 19, 2008, now U.S. Pat. No. 8,457,727, the specification of which is expressly incorporated herein by reference in its entirety.

CROSS REFERENCE TO RELATED APPLICATIONS

The present invention relates to the following commonly assigned applications, each of which is incorporated herein by reference: U.S. patent application Ser. No. 10/186,069, filed Jun. 28, 2002, entitled "Implantable Cardiac Device Having a System for Detecting T-Wave Alternan Patterns and Method," filed Jun. 28, 2002, granted Apr. 11, 2006 as U.S. Pat. No. 7,027,867; U.S. patent application Ser. No. 10/868,240, entitled "Implantable Cardiac Device Providing Rapid Pacing T-wave Alternan Pattern Detection and Method," filed Jun. 14, 2004, granted Jul. 17, 2007 as U.S. Pat. No. 7,027,867; U.S. patent application Ser. No. 11/229,411, entitled "Methods and Systems for Detecting the Presence of T-Wave Alternans," filed Sep. 16, 2005; and U.S. patent application Ser. No. 11/229,410, entitled "Methods and Systems for Detecting the Presence of T-Wave Alternans," filed Sep. 16, 2005.

FIELD OF THE INVENTION

The present invention generally relates to an implantable cardiac device that delivers electrical therapy to a patient's heart. The present invention more particularly relates to such a device capable of detecting T-wave alternan patterns.

BACKGROUND

Electrical alternans relate to the differences in electrical potential at corresponding points between alternate heartbeats. T-wave alternans or alternation is a regular or beat-to-beat variation of the ST-segment or T-wave of an electrocardiogram (ECG) which repeats itself every two beats and has been linked to underlying cardiac instability. Typically, by enumerating all consecutive heart beats of a patient, beats with an odd number are referred to as "odd beats" and beats with an even number are referred to as "even beats." A patient's odd and even heartbeats may exhibit different electrical properties of diagnostic significance which can be detected by an ECG.

The presence of these electrical alternans is significant because patients at increased risk for ventricular arrhythmia's commonly exhibit alternans in the ST-segment and the T-wave of their ECG. Clinicians may therefore use these electrical alternans as a noninvasive marker of vulnerability to ventricular tachyarrhythmias. The term T-wave alternans (TWA) is used broadly to denote electrical alternans such as these. It should be understood that the term encompasses both the alternans of the T-wave segment and the ST-segment of an ECG.

T-wave alternans (TWA) has been demonstrated in many studies as a strong predictor of mortality, independent of left ventricular ejection fraction (LVEF). More specifically, it has become well known that T-wave alternans has predictive value for arrhythmic events such as tachyarrhythmias. Additionally, T-wave alternans has been determined to be an indicator of various forms of disordered ventricular repolarization, including disorders found in patients with cardiomyopathy, mild to moderate heart failure, and congestive heart failure.

T-wave alternans (TWA) may be caused by changes in ion exchange during repolarization. If there is a change in the repolarization mechanism on one beat, the heart attempts to readjust on the following beat. This is manifested as an alternating change in the action potential. In the surface ECG this is seen primarily as an amplitude change. For an implanted medical device such as a cardiac pacemaker, the intracardiac electrogram (IEGM) also shows a change in timing. Thus, the term T-wave as used herein may refer to a portion of the ventricular QRS-T-wave complex that includes the T-wave and the QRS-T segment. The alternating feature of TWA can be detected by examination, for example, of the QT interval, T-wave width, T-wave amplitude and morphology, etc. Whatever the designated portion of the intracardiac electrogram, T-wave alternans refers to an alternating pattern of the wave that can be designated "A-B-A-B-A . . . " where A represents every other cycle and B represents every other alternate cycle. As discussed in the literature, when such an alternating pattern appears, the different rates or forms of repolarization of the ventricular cells are statistically associated with a variety abnormal cardiac conditions. Further, the alternating repolarization pattern can lead to increased instability and consequent cardiac arrhythmias. Thus, the presence of T-wave alternans is recognized as an indicator of risk for ventricular arrhythmia and even sudden cardiac death (SCD).

In the past, detection of T-wave alternan patterns has been performed using surface ECGs. Implementation of such detection has included the measurement, on a beat-to-beat basis, of the micro-volt level changes in the T-wave amplitude from the surface ECG. Then, the long record of time series of T-wave amplitude change is transformed into the frequency domain by Fourier series transformation (FFT). A prominent peak in the FFT at 0.5 Hz would verify the existence of a T-wave alternan pattern.

Unfortunately, the above detection method requires the use of medical equipment that must be operated by medical personnel in a medical facility such as a physician's office. The detection requires long term recording of surface ECGs and off-line analysis with robust computation equipment. As a result, T-wave alternan pattern monitoring has been inconvenient and cumbersome. As a result, it is difficult to provide continuous and regular T-wave alternan pattern monitoring.

Many patients who would benefit from T-wave alternan pattern monitoring have an implanted cardiac device such as an implantable defibrillator or a combined defibrillator pacemaker. It would thus be highly desirable if such an implanted device could monitor for T-wave alternan patterns. However, the prior art detection method does not lend itself for such application due to, for example, the required long term monitoring, surface ECG, and robust computational requirements for Fourier series transformation.

Several studies have demonstrated that the beat by beat alterations (in ECG and EGM recordings) before the onset of VT/VF are significantly different to that in control recordings. These findings support the feasibility of early prediction of arrhythmia occurrence. However, the relationship between the degree of beat by beat alterations prior to VT/VF and the complexity of VT/VF has not been known. Since beat by beat alterations indicate the dynamic instability within the heart, it plays an important role in the maintenance of VT/VF. Therefore, it is useful to predict the complexity of VT/VF by the degree of alterations before the onset of this VT/VF.

T waves in ECGs and IEGMs are a manifestation of the dispersion of repolarization within the heart. Due to the adaptability in repolarization phase, both T wave morphology and the duration between T wave to R wave are different when heart rate changes. Several mathematical formulas have been established and used in ECG data analysis for compensating the effects of heart rate on Q-T interval. However, these equations cannot be directly applied to IEGM signal analysis because of the morphological difference between the two signals caused by recording location as well as the fact that IEGM signals are attenuated by the internal filter in the device.

Recent studies have demonstrated that T wave alternans significantly increased prior to the onset of ventricular arrhythmias in EGM recording. Hence, it might be possible to predict the onset of tachyarrhythmias by continuous T wave alternans monitoring. In order to accurately analyze T wave at various heart rate (including some cases of supraventricular arrhythmias), the device needs to know when the T wave starts and ends.

Despite intensive research, occurrence of ventricular tachycardia (VT) and ventricular fibrillation (VF) remain highly unpredictable. Premature ventricular contraction (PVC) is very common in patients with structural and functional heart diseases. A recent study in MADIT II patients with ICDs revealed that 77% of the stored VFs were initiated by single PVC. This finding suggests that PVCs play an important role in arrhythmia (in particular, VF) initiation.

On the other hand, the probability that PVCs will induce VT/VF is extremely low. For example, a patient has just one PVC per minute will have about half million PVCs per year, but VT/VF episodes in these patients occur over months to years, not minutes. Therefore, it is likely that majority of the PVCs do not happen at a critical vulnerable period except a few of them.

In order for an implanted cardiac device to provide T-wave alternan pattern monitoring, there is a need for a new and different approach. The present invention addresses that need.

BRIEF SUMMARY OF THE INVENTION

In accordance with one embodiment of the invention an approach to prospectively predict the complexity of arrhythmias based on beat by beat alterations before the actual arrhythmia onset is provided. This method provides an early prediction of an arrhythmia and allows for optimizing antiarrhythmia therapy. In this embodiment, the method is used in implantable devices to predict the complexity of coming VT/VF based on beat by beat alterations before the actual onset of VT/VF. The method extracts EGM features and tracks beat by beat alterations. These features may include the amplitude, duration, slope, area under the curve of QRS complex and T wave portion, as well as conduction velocity. Table 1. illustrates some features that can be extracted from ventricular IEGM. Based on the degree of alterations, the method predicts the complexity of VT/VF and selects optimal therapy. For example, reduce the number of ATP attempts when the method predicts high complexity.

In another embodiment of the invention, a heart rate dependent T wave correction which can be used in T wave alternans detection in EGM recordings is disclosed. A general form of the equation is:

$$T = \frac{A}{\left(\frac{\text{Heart Rate}}{B}\right)^k} \quad \text{Eq. 1}$$

For example, the equation below identifies T wave accurately for heart rate ranging from 50 to 160 as provided in FIG. 3 where T wave start and end time from R wave for heart rate ranged from 50 to 160 bpm.

$$T_{start} = \frac{160}{\left(\frac{\text{Heart Rate}}{60}\right)^{0.5}} \quad \text{Eq. 2}$$

$$T_{end} = \frac{480}{\left(\frac{\text{Heart Rate}}{70}\right)^{0.7}} \quad \text{Eq. 3}$$

where $T_{start}$ & $T_{end}$ are the start and end time from the peak of the QRS.

In another embodiment, a method used in implantable devices to identify vulnerability and risk of arrhythmias is disclosed. Once a PVC is detected, several features will be calculated and saved in the device. These features include averaged heart rate before the PVC, premature coupling interval of the PVC, averaged T wave duration before the PVC, and morphological characteristics (amplitude, large negative peak, etc.) of the PVC. The implantable device will also register lethal PVC characteristics if VT/VF (both sustained and non-sustained) is triggered by a PVC. The characteristics of newly detected PVCs will be compared to an existing template to determine the likelihood of arrhythmia initiation. If the chance of arrhythmia initiation is high, a device may respond correspondingly to reduce the chance of arrhythmia initiation through pacing interruption and may start to prepare antiarrhythmia therapy before an arrhythmia happens such as by charging high voltage capacitors.

In another embodiment of the invention provides a time domain method to predict risks of spontaneous VT/VF by tracking beat to beat alterations in extracted EGM features. As an example, Table 1 lists the extracted features from a ventricular EGM recording. Beat to beat alterations in amplitude and pattern from some or all of these extracted features will be fed into a mathematical model to predict risks of arrhythmias.

This invention further consists of a new method to monitor the transition pattern of beat by beat variation of any electrical and mechanical characteristics. These characteristics include but are not limited to intervals (R-R interval, Q-T interval, etc), EGM amplitudes (QRS amplitude, T wave amplitude, etc), and their analogies derived from intracardiac impedance. For any single or combined characteristic, the beat by beat variation will be calculated by subtracting the value associated with the current beat by the value associated with its previous beat.

In one embodiment, the transition pattern of beat to beat variations in IEGM will be calculated by the percentage of reversal point (PRP) within a certain time window based on Eq. 3. PRP value will be used as a risk indicator of arrhythmias.

$$PRP = \frac{\text{number of reversal point within the window} - 2}{\text{total number of beats from the 1st to the last reversal point} - 2} \quad \text{Eq. 3}$$

FIG. 4 shows two examples with A-B (panel A) and A-B-C (panel B) patterns and their corresponding PRP values. The PRP value can be continuously calculated in a moving window and generate detection alarm when the value falls into each block (e.g. PRP 0.9~1 for A-B pattern, PRP 0.62~0.72 for A-B-C pattern). In one method, PRP itself can be used to trigger an alarm of vulnerable period to arrhythmias; in another method, PRP will be combined into a multiple factors determining algorithm to trigger an alarm of vulnerable period to arrhythmias.

The PRP calculation will be corrected when PVC happens within the calculation window. In one approach, PRP calculation will ignore the PVC beats and the beats prior and after each PVC beat; in another approach, the value associated with a PVC beat will be replaced by an averaged value from the non-PVC beats before PRP calculation.

In another embodiment, the continuous oscillation pattern monitoring can be used as an indicator of patient health status and disease progression. If the PRP values within a period (e.g. a month) shows a significant trend of increasing, an alarm indicating heart disease progression or remodeling will be triggered.

In still another embodiment of the invention, a method that automatically calculates T wave start and end time based on the heart rate computed from the previous beat is disclosed. This allows one to truncate a portion from the EGM signals at every heart beat and extract critical features related to T wave instability and correspondingly predicts the onset of ventricular tachyarrhythmias.

Examples of other T-wave metrics that can be measured (i.e., besides T-wave amplitude) include T-wave width, T-wave slope, T-wave area, T-wave morphology, QT interval, and evoked QT interval.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
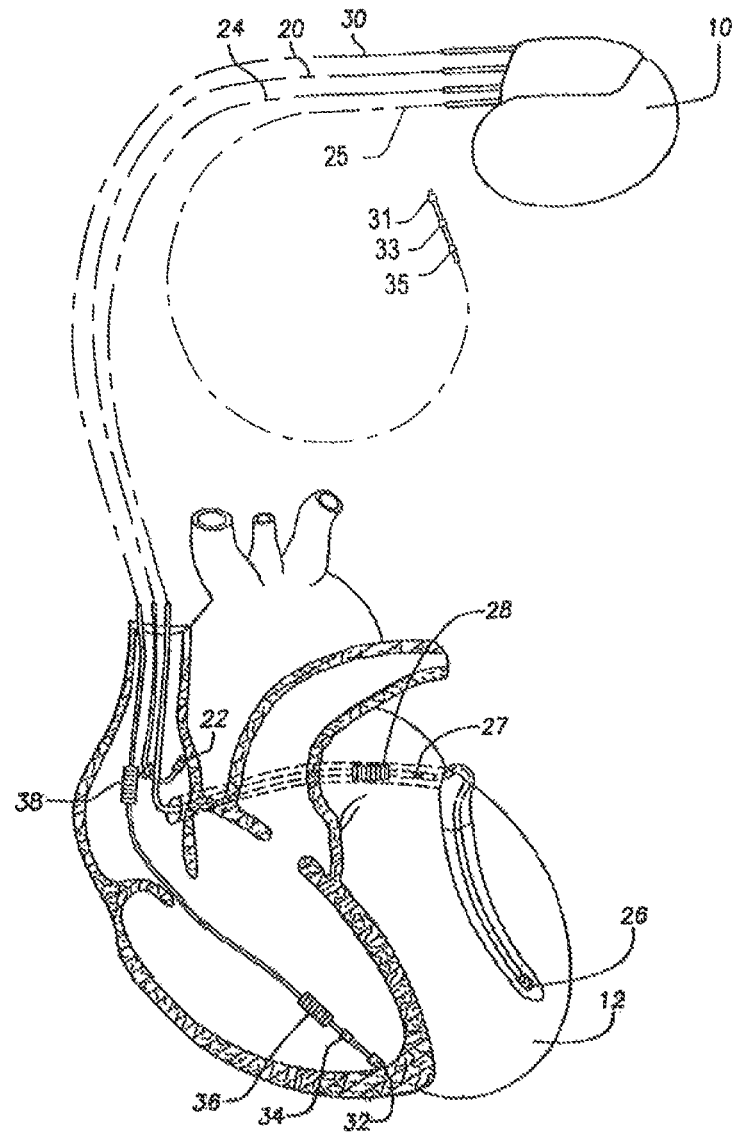
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
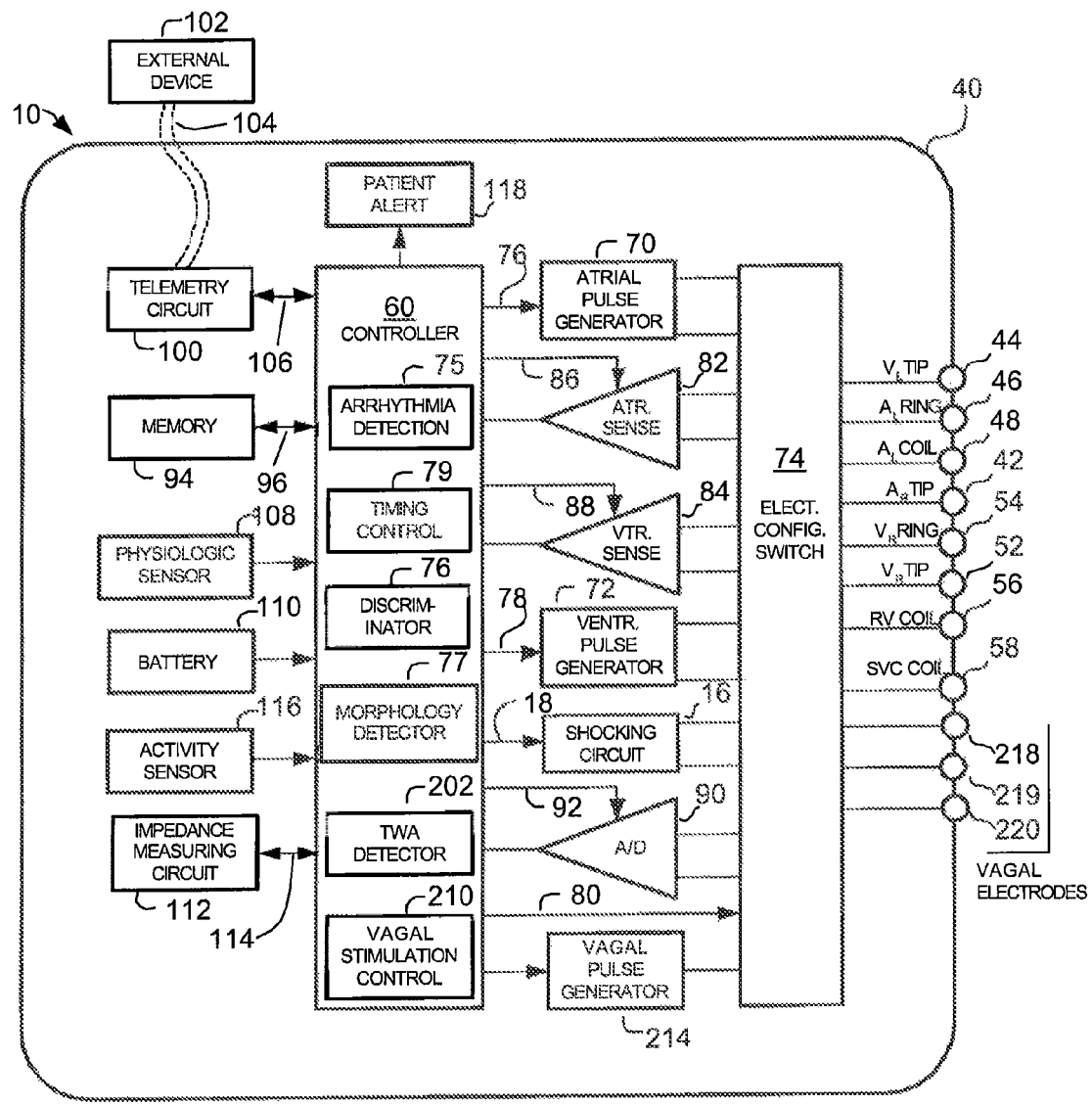
FIG. 2 is a functional block diagram of an exemplary ICD that can provide cardioversion, defibrillation, and pacing stimulation in four chambers of a heart, and detect the presence of T-wave alternans, in accordance with an embodiment of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy.

As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the ICD's and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting T-wave alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (ND) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

TWA Detection

Referring back to FIG. 2, in accordance with embodiments of the present invention, microcontroller 60 includes a T-wave alternan (TWA) detector 202, which as described in more detail below, can detect the presence of T-wave alternans. The TWA detector 202 can be implemented within the microcontroller 60, as shown in FIG. 2. Thus, TWA detector 202 can be implemented by software, firmware, or combinations thereof. It is also possible that all, or portions, of TWA detector 202 can be implemented using hardware. Further, it is possible that all, or portions, of TWA detector 202 be implemented external to the microcontroller 60.

In an embodiment, TWA detector 202 triggers data acquisition circuit 90 and timing control circuit 79 to record IEGM signal information following intrinsic, induced or simulated premature contractions of the ventricles. TWA detector 202 can measure T-wave metrics, such as T-wave amplitude, T-wave amplitude, T-wave width, T-wave slope, T-wave area, T-wave morphology, QT interval, evoked QT interval, etc. in the IEGM signal generated by the sensing circuits of the data acquisition system 90. TWA detector 202 can also trigger implantable device 10 to respond appropriately when T-wave alternans are detected, as will be explained in more detail below. Additionally, in conjunction with a telemetry circuit 100, TWA detector 202 can be configured to deliver status information, relating to the patient's T-wave alternans, to an external device 102 through an established communication link 104, TWA detector 202 may also trigger a patient or physician alert in response to detecting T-wave alternans. For example, a patient alert 118, which produces a vibratory or auditory alert, may be triggered by the TWA detector 202.

T-wave alternans have been demonstrated in many studies to be strong predictor of mortality, independent of left ventricular ejection fraction (LVEF). It has been generally believed that an elevated constant heart rate is a requirement for the detection of T-wave alternans. However, a recent work published by Bullinga et al., entitled "Resonant Pacing Improves T-wave Alternans Testing in Patients with Dilated Cardiomyopathy" (Heart Rhythm v1:S129, 2004) revealed a more robust detection with "resonant pacing" scheme. In this technique, TWA with higher amplitudes were detected by pacing at a relatively shorter interval periodically once every fourth cycle during a moderately fast and constant pacing routine. However, Bullinga's scheme still requires that a patient be paced at an elevated heart rate, which for various reasons is not always desirable. Additionally, in Bullinga's technique the heart is perturbed continuously for a certain period in order to get a response, and then the response is scaled and translated into myocardial stability.

It is believed that T-wave amplitudes will also be elevated following intrinsic premature contractions of the ventricles when the myocardium is electrically unstable, and thus, that T-wave alternans can be detected by monitoring T-waves in a predetermined number of beats (e.g., 2 to 10 beats) that follow intrinsic premature contractions of the ventricles. While these embodiments of the present invention can be used even when there is not a moderately fast and/or constant pacing routine, they can also be used when intrinsic premature ventricular contractions occur during a pacing routing (at normal or moderately fast rates). Additionally, the techniques of the present invention can also be used when a patient's intrinsic heart rate is not elevated, as well as when a patient's intrinsic heart rate is elevated.

As mentioned above, T-wave alternans are a known predictor of arrhythmic events such as tachyarrhythmias. Accordingly, in an embodiment, a patient is alerted (e.g., using alert 118) when T-wave alternans are detected. Such an alert could be a vibratory or auditory alert that originates from within the implantable device 10. Alternatively, the implantable device 10 may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible the a tachyarrhythmia may be avoided, or if it does occur, the patient will be less dangerous to themselves and others if the patient is resting when the tachyarrhythmias occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever the presence of T-wave alternans is detected.

In further embodiments, therapy can be triggered in response to detecting the presence of T-wave alternans. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate drug therapy. In still another embodiment, the implanted device, if appropriately equipped, can deliver appropriate pacing therapy. In still another embodiment, the implantable device, if cable of delivering shock therapy, can begin to charge its capacitors in case the patient goes into ventricular fibrillation and needs shock therapy. These are just a few examples of the types of responses that can be performed upon detection of T-wave alternans. One of ordinary skill in the art would understand from the above description that other response are also possible, while still being within the spirit and scope of the present invention.

An advantage of the embodiments of the present invention is that these embodiments can be performed by an implantable device (such as an implantable monitoring device) that does not include stimulation capabilities. This, however, does not mean that these embodiments can not be implemented by an implantable device that does provide for stimulation capabilities, as can be appreciated from the above discussion. Another advantage of these embodiments is that they enable T-wave alternans to be monitored for without requiring elevation of a patient's heart rate through exercise or overdrive pacing. In other words, with embodiments of the present invention the state of a heart can be assessed in its sort of native and un-paced state. This is especially advantageous with patients that are for whatever reason physically incapacitated or limited such that elevating their heart rate would be difficult and/or dangerous. Nevertheless, as stated above, these embodiments can also be used if a patient's heart happens to be elevated.

One response can be to store information related to the metrics of T-waves for later retrieval and/or transmission to a physician or other clinician. Another response involves triggering a patient or physician alert that warns of an impending arrhythmia, thereby allowing the patient to respond appropriately. Such an alert could be, e.g., a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. Additionally or alternatively, the patient can be instructed to take medication when alerted. In further embodiments, a preventive therapy can be triggered in response to assessing a risk of an impending arrhythmia. One type of therapy would be for an implanted device (e.g., device 10) to stimulate the vagal nerve, in an attempt to slow down the heart rate. Another response would be to deliver an appropriate anti-arrhythmia pacing therapy. In another embodiment, the implanted device, if appropriately equipped, can deliver an appropriate drug therapy. One of ordinary skill in the art would appreciate from the above description that other types of therapies can be triggered. These are just a few examples of the types of responses that can be performed upon assessing a risk of an impending arrhythmia. One of ordinary skill in the art would understand from the above description that other responses are also possible, while still being within the spirit and scope of the present invention.

In further embodiments, changes in magnitudes of alternation are tracked thereby track changes in myocardial electrical stability. This can include recognizing increases in magnitudes of alternations as being indicative of increased electrical instability of the myocardium, and recognizing decreases in magnitudes of alternations as being indicative of increased electrical stability of the myocardium.

In accordance with one embodiment of the invention an approach to prospectively predict the complexity of arrhythmias based on beat by beat alterations before the actual arrhythmia onset is provided. This method provides an early prediction of an arrhythmia and allows for optimizing antiarrhythmic therapy. In this embodiment, the method is used in implantable devices to predict the complexity of coming VT/VF based on beat by beat alterations before the actual onset of VT/VF. The method extracts EGM features and tracks beat by beat alterations. These features may include the amplitude, duration, slope, area under the curve of QRS complex and T wave portion, as well as conduction velocity. Table 1. provides some features that can be extracted from ventricular IEGM. Based on the degree of alterations, the method predicts the complexity of VT/VF and selects optimal therapy. For example, the device can be programmed to reduce the number of ATP attempts when the method predicts high complexity. Alternatively, ATP can be skipped altogether and the device can move tachyarrhythmia therapy directly to cardioversion shocks.

TABLE 1

| No. | Feature | Description |
| --- | --- | --- |
| 1 | Heart Rate | Calculated based on Beat to Beat RR interval |
| 2 | Rpeak2peak | QRS peak to peak Amplitude (Amplitude from C to F) |
| 3 | Rtime1 = QRStime1 | Timing between maximum slope to negative QRS Peak (B to F) |
| 4 | Rtime2 = QRStime2 | Timing between maximum slope to minimum slope in QRS (B to D) |
| 5 | Rtime3 = QRStime3 | Timing between 2 Zero Crossing in QRS (A to E) |
| 6 | Tpeak2peak | T wave peak to peak Amplitude (Amplitude from I to G) |
| 7 | Tpeaktime | Timing between QRS and Tpeak (C to I) |
| 8 | Tpeaktime_Bazett | Tpeaktime corrected by Bazett equation: Tpeaktime/sqrt (RR-interval) |

TABLE 1-continued

| No. | Feature | Description |
|---|---|---|
| 9 | Tpeaktime_Hodges | Tpeaktime corrected by Hodges equation: Tpeaktime + (1.75 * (current beat HR-60)) |
| 10 | Tmaxslope | Maximum Slope in T wave (Value at H) |
| 11 | Tmaxslope_time | Timing between QRS and max T slope (C to H) |
| 12 | Tminslope | Minimum Slope in T wave (Value at J) |
| 13 | Tminslope_time | Timing between QRS and min T slope (C to J) |
| 14 | Tarea | Area under T wave |
| 15 | Ttime1 | T wave duration calculated by corrected Start and End of T wave |
| 16 | Ttime2 | Timing between max and min slope in T wave (H to J) |
| 17 | Ttime3 | Timing between 2 Zero Crossing in T wave (H to K) |

In some embodiments, it is desirable to use a heart rate dependent T wave correction which can be used in T wave alternans detection in EGM recordings. A general form of the equation is:

$$T = \frac{A}{\left(\frac{\text{Heart Rate}}{B}\right)^k} \quad \text{Eq. 1}$$

Figure 3:
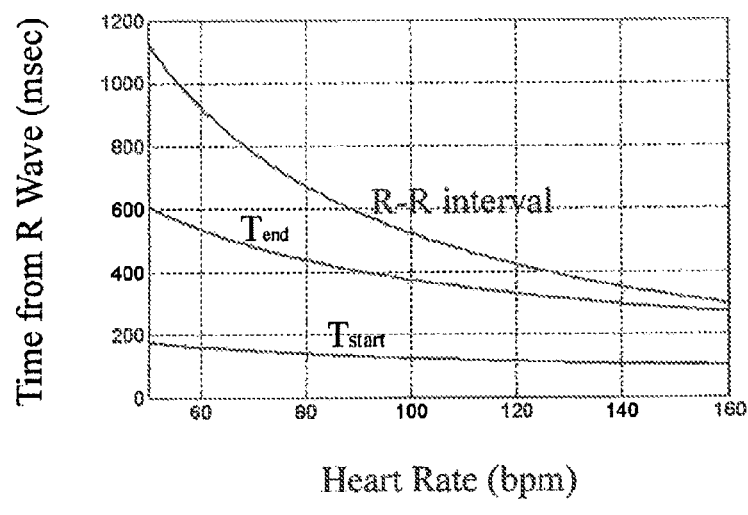
FIG. 3 is a graph illustrating the relationship between the start and end of the T-wave from the R-wave as a function of heart rate.

For example, the equations below identify the start and end of T waves accurately for heart rates ranging from 50 to 160 bom as provided in FIG. 3 where T wave start and end time from R wave for heart rate ranged from 50 to 160 bpm.

$$T_{start} = \frac{160}{\left(\frac{\text{Heart Rate}}{60}\right)^{0.5}} \quad \text{Eq. 2}$$

$$T_{end} = \frac{480}{\left(\frac{\text{Heart Rate}}{70}\right)^{0.7}} \quad \text{Eq. 3}$$

where $T_{start}$ & $T_{end}$ are the start and end time from the peak of the QRS.

Another embodiment of the invention involves a method used in implantable devices to identify vulnerability and risk of arrhythmias. Once a PVC is detected, several features are calculated and saved in the device. These features include averaged heart rate before the PVC, premature coupling interval of the PVC, averaged T wave duration before the PVC, and morphological characteristics (amplitude, large negative peak, etc.) of the PVC. The implantable device also registers lethal PVC characteristics if VT/VF (both sustained and non-sustained) is triggered by a PVC. The characteristics of newly detected PVCs will be compared to an existing template to determine the likelihood of arrhythmia initiation. If the chance of arrhythmia initiation is high, the device can respond correspondingly to reduce the chance of arrhythmia initiation through pacing interruption and may start to prepare antiarrhythmia therapy before an arrhythmia happens such as by charging high voltage capacitors.

In another embodiment of the invention a time domain method is used to predict risks of spontaneous VT/VF by tracking beat to beat alterations in extracted EGM features. As an example, Table 1 lists the extracted features from a ventricular EGM recording. Beat to beat alterations in amplitude and pattern from some or all of these extracted features will be fed into a mathematical model to predict risks of arrhythmias.

This invention further consists of a new method to monitor the transition pattern of beat by beat variation of any electrical and mechanical characteristics. These characteristics include but are not limited to intervals (R-R interval, Q-T interval, etc), EGM amplitudes (QRS amplitude, T wave amplitude, etc), and their analogies derived from intracardiac impedance. For any single or combined characteristic, the beat by beat variation will be calculated by subtracting the value associated with the current beat by the value associated with its previous beat.

Further, the transition pattern of beat to beat variations in IEGM can be calculated by the percentage of reversal point (PRP) within a certain time window based on Eq. 3. PRP value will be used as a risk indicator of arrhythmias.

$$PRP = \frac{\text{number of reversal point within the window} - 2}{\text{total number of beats from the 1st to the last reversal point} - 2} \quad \text{Eq. 3}$$

Figure 4:
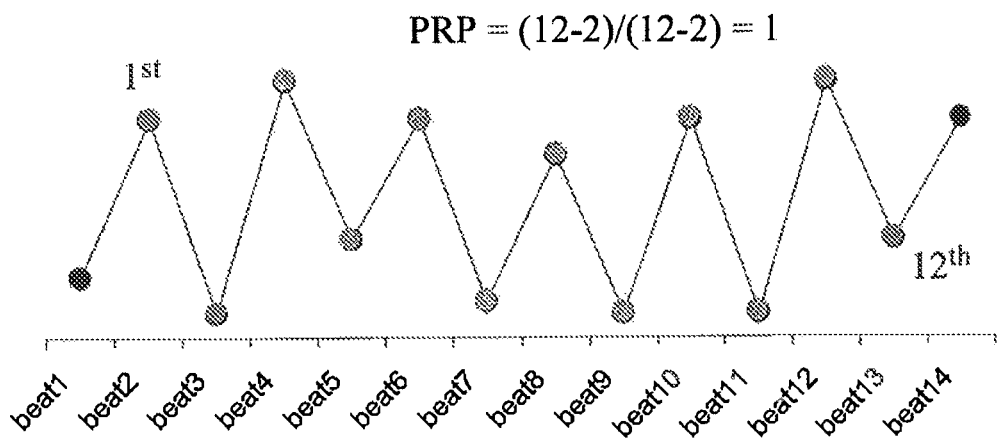
FIG. 4 shows two examples of alternans patterns and their corresponding PRP values.
Figure 4:
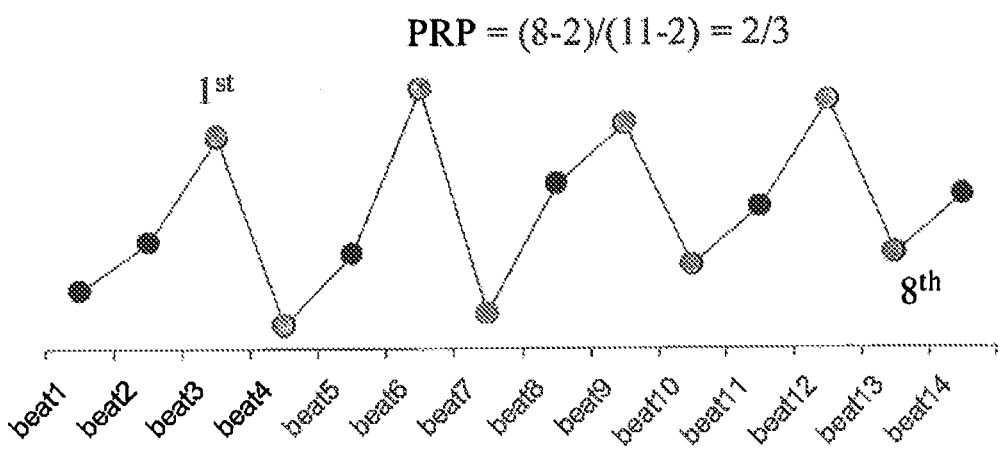

FIG. 4 shows two examples with A-B (panel A) and A-B-C (panel B) patterns and their corresponding PRP values. The PRP value can be continuously calculated in a moving window and generate detection alarm when the value fails into each block (e.g. PRP 0.9~1 for A-B pattern, PRP 0.62~0.72 for A-B-C pattern). In one method, PRP itself can be used to trigger an alarm of vulnerable period to arrhythmias; in another method, PRP will be combined into a multiple factors determining algorithm to trigger an alarm of vulnerable period to arrhythmias.

The PRP calculation can be corrected when a PVC happens within the calculation window. In one approach, PRP calculation will ignore the PVC beats and the beats prior and after each PVC beat. In another approach, the value associated with a PVC beat will be replaced by an averaged value from the non-PVC beats before PRP calculation.

In another embodiment, the continuous oscillation pattern monitoring can be used as an indicator of patient health status and disease progression. If the PRP values within a period (e.g. a month) shows a significant trend of increasing, an alarm indicating heart disease progression or remodeling will be triggered.

In still another embodiment of the invention, a method that automatically calculates T wave start and end time based on the heart rate computed from the previous beat is disclosed. This allows one to truncate a portion from the EGM signals at every heart beat and extract critical features related to T wave instability and correspondingly predicts the onset of ventricular tachyarrhythmias.

Figure 5:
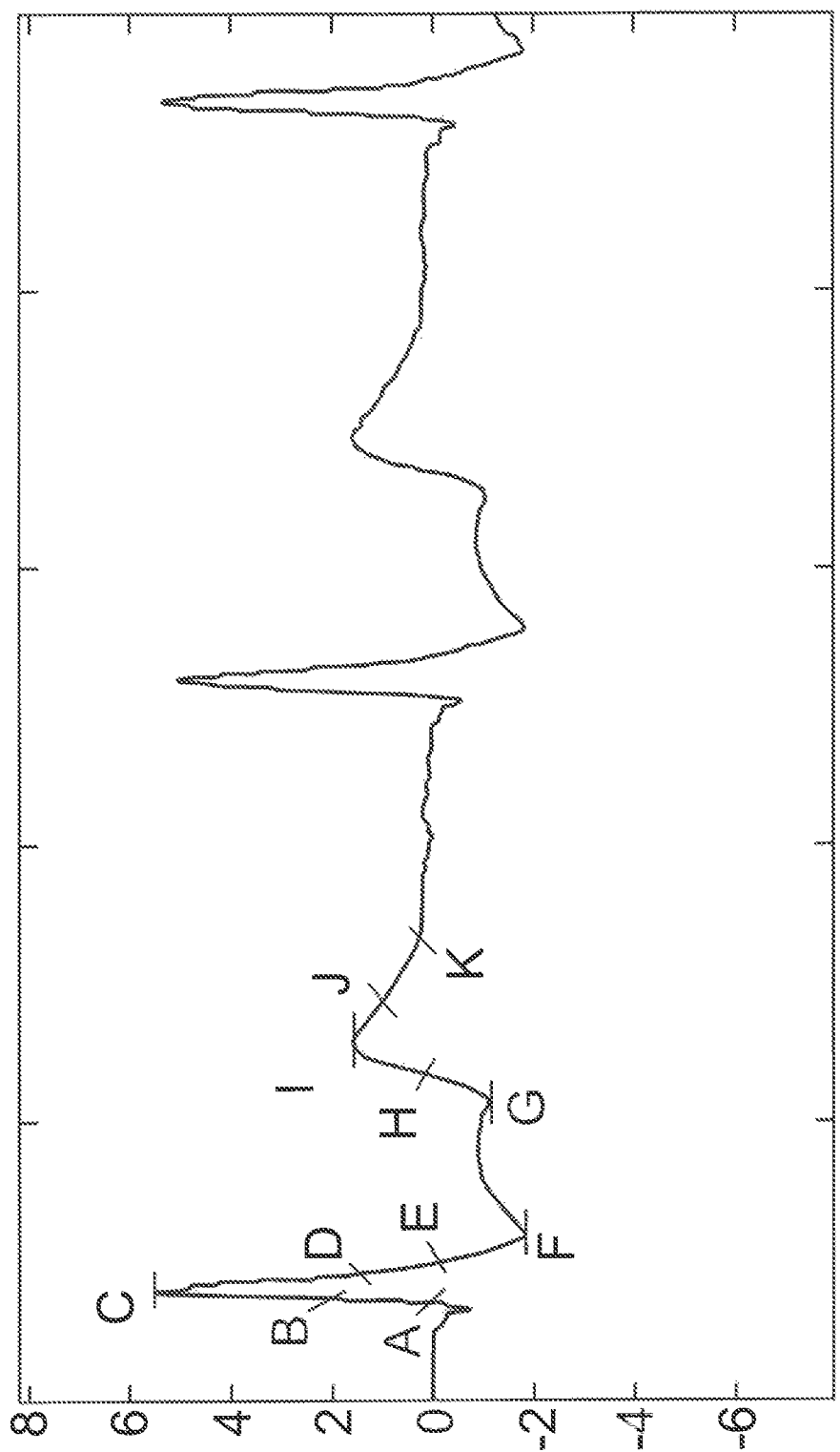
FIG. 5 shows the points that can be monitored in a sensed or stored EGM.

Referring now to FIG. 5, various points in the sensed EGM that may be useful in practicing the invention are illustrated. In the FIG. 5, the following points represent the time at A=Zero Crossing1 for QRS
B=Maximum Slope for QRS
C=Positive Peak for QRS
D=Minimum Slope for QRS
E® Zero Crossing2 for QRS
F=Negative Peak for QRS
G=Negative Peak for T wave
H=Zero Crossing1 for T wave, Maximum Slope for T wave (only here. In actual beat, it may or may not be same)
I=Positive Peak for T wave
J=Minimum Slope for T wave
K=Zero Crossing2 for T wave FIG. 3 provides an example of using the percentage of reversal point (PRP) to identify A) A-B patterned oscillation and B) A-B-C patterned oscillation. Green circles are the reversal points. PRP is equal to one in A-B patterned oscillation, and ⅔ (=0.67) in A-B-C patterned oscillation.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the claims and their equivalents.

What is claimed is:

1. A non-transitory computer readable storage medium for a computing device having a memory and a microcontroller, the non-transitory computer readable storage medium comprising instructions to:
   obtain a physiological parameter representative of myocardial behavior within a time window;
   count a number of reversal points in values of the physiological parameter within the time window;
   calculate a percentage of reversal points (PRP) within the time window; and
   identify myocardial instability based on the PRP.

2. The non-transitory computer readable storage medium of claim 1, wherein the instructions direct the microcontroller to:
   calculate the PRP within the time window using the equation:

$$PRP = \frac{\text{number of reversal point within the window} - 2}{\text{total number of beats from the 1st to the last reversal point} - 2},$$

and
identify the PRP as a risk indicator of arrhythmia.

3. The non-transitory computer readable storage medium of claim 1, wherein the instructions direct the microcontroller to initiate a responsive action when myocardial instability is identified.

4. The non-transitory computer readable storage medium of claim 1, wherein each of the reversal points corresponds to a point where a value of the physiological parameter for a cardiac cycle:
   exceeds a value of the physiological parameter for an immediately preceding cardiac cycle and exceeds a value of the physiological parameter for an immediately subsequent cardiac cycle, or
   is less than a value of the physiological parameter for an immediately preceding cardiac cycle and is less than a value of the physiological parameter for an immediately subsequent cardiac cycle.

5. The non-transitory computer readable storage medium of claim 1, wherein the physiologic parameter represents at least one of a Q-T interval, QRS amplitude, P-wave amplitude, T-wave amplitude or R-R interval.

6. A device for analyzing myocardial instability, the device comprising:
   a memory that stores a physiological parameter representative of myocardial behavior within a time window; and
   a microcontroller that counts a number of reversal points in values of the physiological parameter within the time window;
   wherein microcontroller also calculates a percentage of reversal points (PRP) within the time window, and identifies myocardial instability based on the PRP.

7. The device of claim 6, wherein the microcontroller calculates the PRP within the time window using the equation:

$$PRP = \frac{\text{number of reversal point within the window} - 2}{\text{total number of beats from the 1st to the last reversal point} - 2},$$

and
wherein the microcontroller uses the PRP as a risk indicator of arrhythmia.

8. The device of claim 6, wherein the microcontroller initiates a responsive action when myocardial instability is identified.

9. The device of claim 6, wherein each of the reversal points corresponds to a point where a value of the physiological parameter for a cardiac cycle:
   exceeds a value of the physiological parameter for an immediately preceding cardiac cycle and exceeds a value of the physiological parameter for an immediately subsequent cardiac cycle, or
   is less than a value of the physiological parameter for an immediately preceding cardiac cycle and is less than a value of the physiological parameter for an immediately subsequent cardiac cycle.

10. The device of claim 6, wherein the physiologic parameter represent at least one of a Q-T interval, QRS amplitude, P-wave amplitude, T-wave amplitude or R-R interval.

* * * * *